United States Patent
Maruyama et al.

(10) Patent No.: US 12,284,455 B2
(45) Date of Patent: Apr. 22, 2025

(54) OPTICAL MEASUREMENT DEVICE AND OPTICAL MEASUREMENT SYSTEM

(71) Applicant: SONY GROUP CORPORATION, Tokyo (JP)

(72) Inventors: Tsutomu Maruyama, Tokyo (JP); Masaaki Hara, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 312 days.

(21) Appl. No.: 17/620,102

(22) PCT Filed: Jun. 16, 2020

(86) PCT No.: PCT/JP2020/023499
§ 371 (c)(1),
(2) Date: Dec. 16, 2021

(87) PCT Pub. No.: WO2020/262092
PCT Pub. Date: Dec. 30, 2020

(65) Prior Publication Data
US 2022/0247962 A1    Aug. 4, 2022

(30) Foreign Application Priority Data
Jun. 26, 2019   (JP) .................................. 2019-119128

(51) Int. Cl.
*H04N 25/77* (2023.01)
*G01N 15/14* (2006.01)
(Continued)

(52) U.S. Cl.
CPC .............. *H04N 25/77* (2023.01); *G01N 15/14* (2013.01); *G01N 21/64* (2013.01); *H04N 23/56* (2023.01); *G01N 15/01* (2024.01)

(58) Field of Classification Search
CPC ........ H04N 25/77; H04N 23/56; G01N 15/14; G01N 21/64; G01N 2015/0065
See application file for complete search history.

(56) References Cited

U.S. PATENT DOCUMENTS

| 5,272,354 A | 12/1993 | Kosaka |
| 2014/0339446 A1 | 11/2014 | Yamamoto et al. |

(Continued)

FOREIGN PATENT DOCUMENTS

| CN | 108139268 A | 6/2018 |
| CN | 108370424 A | 8/2018 |

(Continued)

OTHER PUBLICATIONS

International Search Report and Written Opinion of PCT Application No. PCT/JP2020/023499, issued on Sep. 1, 2020, 11 pages of ISRWO.

(Continued)

*Primary Examiner* — Sunghyoun Park
(74) *Attorney, Agent, or Firm* — CHIP LAW GROUP

(57) ABSTRACT

There is provided an optical measurement device including a spectral optical system that disperses fluorescence emitted from a biological specimen, and an image sensor that receives the fluorescence dispersed by the spectral optical system and generates fluorescence information. The image sensor is divided into a plurality of regions that receive different wavelength components of the fluorescence and generate fluorescence information for each of the wavelength components.

10 Claims, 9 Drawing Sheets

(51) Int. Cl.
*G01N 21/64* (2006.01)
*H04N 23/56* (2023.01)
*G01N 15/01* (2024.01)

(56) References Cited

U.S. PATENT DOCUMENTS

| | | | |
|---|---|---|---|
| 2015/0141268 A1* | 5/2015 | Rothberg | C12Q 1/6874 438/22 |
| 2016/0161410 A1* | 6/2016 | Keller | G02B 21/362 435/287.3 |
| 2017/0328826 A1 | 11/2017 | Diebold et al. | |
| 2018/0231452 A1 | 8/2018 | Ren et al. | |
| 2018/0328783 A1 | 11/2018 | Nishihara et al. | |
| 2018/0348381 A1 | 12/2018 | Nishihara et al. | |
| 2019/0049374 A1 | 2/2019 | Nishihara et al. | |
| 2019/0154850 A1 | 5/2019 | Nishihara et al. | |
| 2019/0204577 A1* | 7/2019 | Faris | H04N 23/67 |

FOREIGN PATENT DOCUMENTS

| | | |
|---|---|---|
| CN | 109477784 A | 3/2019 |
| EP | 0543514 A2 | 5/1993 |
| EP | 2997348 A1 | 3/2016 |
| EP | 3455608 A1 | 3/2019 |
| EP | 3489723 A1 | 5/2019 |
| JP | 05-142137 A | 6/1993 |
| JP | 2007-113979 A | 5/2007 |
| JP | 2007-285999 A | 11/2007 |
| JP | 2009230021 A | 10/2009 |
| JP | 2016-524703 A | 8/2016 |
| JP | 2017-058361 A | 3/2017 |
| JP | 2018-013422 A | 1/2018 |
| KR | 10-2019-0006164 A | 1/2019 |
| WO | 2014/186461 A1 | 11/2014 |
| WO | 2017/011549 A1 | 1/2017 |
| WO | 2017/086181 A1 | 5/2017 |
| WO | 2017/104438 A1 | 6/2017 |
| WO | 2017/145816 A1 | 8/2017 |
| WO | 2017/197271 A1 | 11/2017 |
| WO | 2018/016345 A1 | 1/2018 |

OTHER PUBLICATIONS

"Quantification of cellular properties using a flow cytometer", Safety of IPS cell and high quality manufacturing technology, Chapter 5, Section 6, Oct. 31, 2016, pp. 327-337.

\* cited by examiner

OPTICAL MEASUREMENT DEVICE AND OPTICAL MEASUREMENT SYSTEM

CROSS REFERENCE TO RELATED APPLICATIONS

This application is a U.S. National Phase of International Patent Application No. PCT/JP2020/023499 filed Jun. 16, 2020, which claims priority benefit of Japanese Patent Application No. JP 2019-119128 filed in the Japan Patent Office on Jun. 26, 2019. Each of the above-referenced applications is hereby incorporated herein by reference in its entirety.

FIELD

The present disclosure relates to an optical measurement device and an optical measurement system.

BACKGROUND

Conventionally, there is flow cytometry as a method for analyzing proteins of biologically relevant microparticles such as cells, microorganisms, and liposomes. A device used for the flow cytometry is referred to as a flow cytometer (FCM). In the flow cytometer, microparticles flowing in a flow path in a line are irradiated with laser light having a specific wavelength, light such as fluorescence, forward scattered light, and side scattered light emitted from each microparticle is converted into an electrical signal by a photodetector and quantified, and the result is statistically analyzed, thereby determining the type, size, structure, and the like of each microparticle.

In addition, in recent years, a flow cytometer capable of multicolor analysis using a plurality of fluorescent dyes has been developed on the basis of the requests of basic medicine and clinical fields.

CITATION LIST

Patent Literature

Patent Literature 1: JP 2017-58361 A

SUMMARY

Technical Problem

However, in the conventional flow cytometer, since a photomultiplier tube is used as the photodetector, there is a problem that a device configuration in a case where the multicolor analysis is enabled is upsized.

Therefore, the present disclosure proposes an optical measurement device and an optical measurement system that enable multicolor analysis while suppressing upsizing.

Solution to Problem

To solve the above-described problem, an optical measurement device according to one aspect of the present disclosure comprises: a spectral optical system that disperses fluorescence emitted from a biological specimen; and an image sensor that receives the fluorescence dispersed by the spectral optical system and generates fluorescence information, wherein the image sensor is divided into a plurality of regions that receive different wavelength components of the fluorescence and generate fluorescence information for each of the wavelength components.

DESCRIPTION OF EMBODIMENTS

Figure 1:
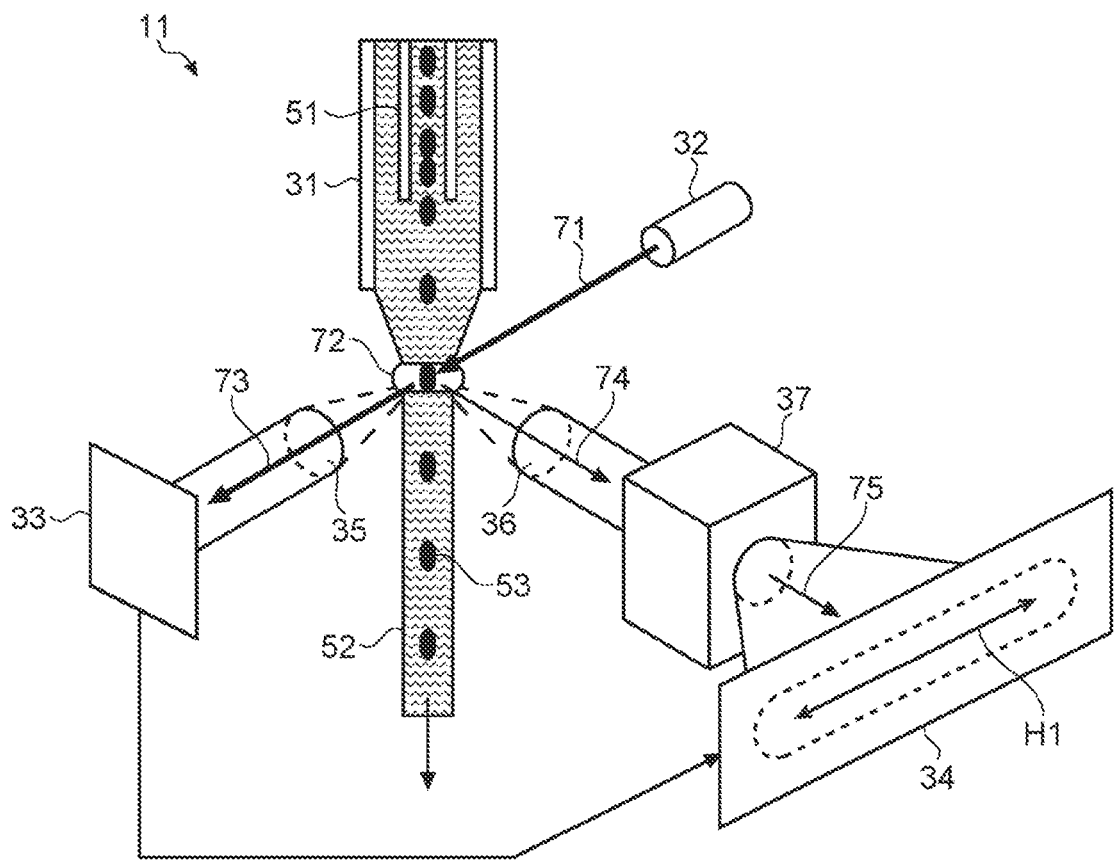
FIG. 1 is a schematic diagram illustrating a schematic configuration example of a flow cytometer according to a first embodiment.

Hereinafter, an embodiment of the present disclosure will be described in detail on the basis of the drawings. Note that, in the following embodiment, the same parts are denoted by the same reference numerals, and redundant description is omitted.

In addition, the present disclosure will be described according to the following item order.

1. Introduction
2. First Embodiment
    2.1 Schematic configuration example of flow cytometer
    2.2 Configuration example of image sensor
    2.3 Circuit configuration example of pixel
    2.4 Operation example of pixel
        2.4.1 Modification of pixel operation
    2.5 Operation example of pulsed light detection
    2.6 Example of relation between position on pixel array unit and wavelength of dispersed light 2.7 Case where image sensor is multichannelized
2.8 Case where virtual filter function is realized by image sensor
2.9 Function and effect
3. Second Embodiment 1. Introduction In multicolor analysis using a plurality of fluorescent dyes (also referred to as fluorescent markers) in one measurement among analyses using a flow cytometer, light from a fluorescent marker other than a target may leak to each photodetector, and analysis accuracy may be deteriorated. Therefore, in a conventional flow cytometer, fluorescence correction is performed in order to extract only target light information from a target fluorescent marker, but in a case of fluorescent markers whose spectra are close to each other, since leakage to a photodetector increases, a problem that the fluorescence correction cannot be performed well may occur.

In order to solve such a problem, a so-called spectral type flow cytometer that acquires and analyzes a fluorescence spectrum has been developed. In the spectral type flow cytometer, fluorescence measured from microparticles (also referred to as specimens or biological specimens) is extracted using spectrum information of fluorescence markers used for dyeing, so that a fluorescence amount of each microparticle is analyzed.

The spectral type flow cytometer is provided with an array type photodetector for spectrum detection instead of the same number of photodetectors as fluorescent markers arranged in the conventional flow cytometer.

In the array type photodetector, for example, a multichannel PMT in which a plurality of photomultiplier tubes are arranged in an array is used. The number of channels of the multichannel PMT is determined on the basis of the wavelength width and wavelength resolution necessary for reproducing all fluorescence spectrum information excited by laser light having a certain wavelength. For example, when it is assumed that the wavelength width necessary for reproducing the fluorescence spectrum information is about 300 nm, which is 500 to 800 nm, and the necessary wavelength resolution is about 9 to 10 nm, the number of channels of the multichannel PMT is set to about 30 to 32 channels.

Although the wavelength width and the wavelength resolution can be changed to some extent by optical design, it is difficult to easily change the wavelength width and the wavelength resolution after the device is commercialized because optical adjustment and the like are required.

In addition, as a function for analyzing fluorescence spectrum information acquired by the spectral type flow cytometer, there is a so-called virtual filter function in which a plurality of channels corresponding to optimum wavelength widths for fluorescence from each fluorescence marker are collectively subjected to signal processing on software to reproduce an optical filter in a pseudo manner. However, in a case where the multichannel PMT described above is used, since an allowable value of the wavelength width of each virtual filter becomes a discrete value due to wavelength resolution determined from the wavelength width necessary for reproducing the fluorescence spectrum information and the number of channels that can be realized by the multichannel PMT, it is difficult to faithfully reproduce characteristics of the optical filter.

Therefore, in the following embodiment, a two-dimensional image sensor is used in the array type photodetector. Since the two-dimensional image sensor is smaller than the multichannel PMT, the overall device scale can be reduced.

In addition, since the two-dimensional image sensor includes more detection units than the multichannel PMT, it is possible to acquire fluorescence spectrum information having fine wavelength resolution and high resolution. Therefore, it is possible to enhance the reproducibility of optical filter characteristics.

Furthermore, since it is possible to add pixel values at an arbitrary wavelength width by using the two-dimensional image sensor, there is also an advantage that it is easy to change the design after productization, such as an increase or decrease in the number of channels or a change in the channel width when the multichannel analysis is performed, an increase or decrease in the number of filters when the virtual filter function is used, or a change in the center wavelength/wavelength width of each filter.

2. First Embodiment

First, an optical measurement device and an optical measurement system according to a first embodiment will be described in detail with reference to the drawings. In the present embodiment, a single spot type flow cytometer will be described as an example, but a flow cytometer according to the present disclosure is not limited to the single spot type, and may be various flow cytometers such as a multispot type. Note that the single spot type means that there is one irradiation spot of laser light (excitation light), and the multispot type means that there are a plurality of irradiation spots. Further, the flow cytometer is classified into a cell analyzer type and a cell sorter type depending on whether or not the flow cytometer has a function of separating a specimen after inspection, but the flow cytometer according to the present embodiment may be any one of the cell analyzer type and the cell sorter type.

2.1 Schematic Configuration Example of Flow Cytometer

Figure 2:
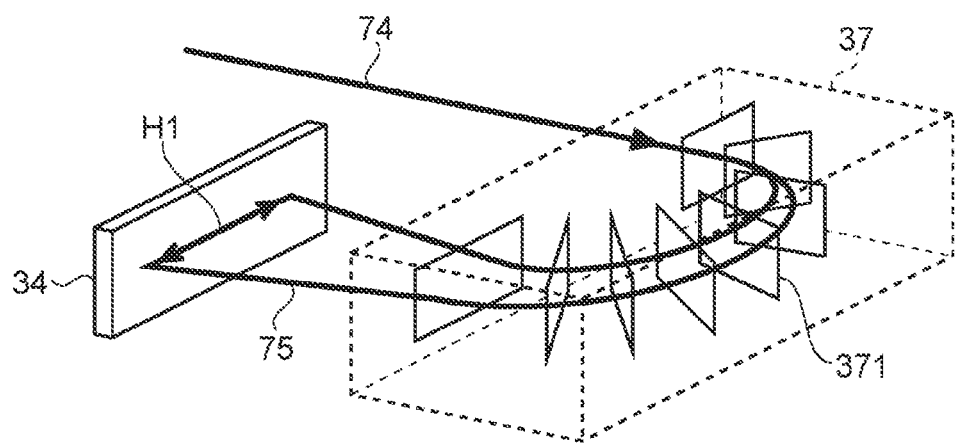
FIG. 2 is a schematic diagram illustrating an example of a spectral optical system in FIG. 1.

FIG. 1 is a schematic diagram illustrating a schematic configuration example of a flow cytometer as an optical measurement device or an optical measurement system according to the first embodiment. FIG. 2 is a schematic diagram illustrating an example of a spectral optical system in FIG. 1.

As illustrated in FIG. 1, a flow cytometer 11 includes a flow cell 31, an excitation light source 32, a photodiode 33, a spectral optical system 37, an individual imaging element (hereinafter, referred to as an image sensor) 34, and condenser lenses 35 and 36.

The cylindrical flow cell 31 is provided above in the drawing, and a sample tube 51 is inserted substantially coaxially into the flow cell 31. The flow cell 31 is a flow path through which specimens 53 flow and has a structure in which a sample flow 52 flows downward in the drawing, and the specimens 53 including cells and the like are released from the sample tube 51. The specimens 53 flow down in a line on the sample flow 52 in the flow cell 31.

The excitation light source 32 is, for example, a laser light source that emits excitation light 71 having a single wavelength, and irradiates an irradiation spot 72 set at a position through which the specimen 53 passes with the excitation light 71. The excitation light 71 may be continuous light or pulsed light having a long time width to some extent.

If the specimen 53 is irradiated with the excitation light 71 at the irradiation spot 72, scattering of the excitation light 71 by the specimen 53 or excitation of the specimen 53, a fluorescent marker attached thereto, or the like occurs.

In the present description, a component directed in a direction opposite to the excitation light source 32 with the irradiation spot 72 therebetween in scattered light scattered by the specimen 53 is referred to as forward scattered light 73. Note that the scattered light also includes a component directed in a direction deviated from a straight line connecting the excitation light source 32 and the irradiation spot 72, or a component directed from the irradiation spot 72 to the excitation light source 32. In the present description, in the scattered light, a component directed in a predetermined direction (hereinafter, referred to as the side) deviated from a straight line connecting the excitation light source 32 and the irradiation spot 72 is referred to as side scattered light, and a component directed from the irradiation spot 72 to the excitation light source 32 is referred to as back scattered light.

Further, when the specimen 53, the fluorescent marker, or the like that has been excited is de-excited, fluorescence having a wavelength unique to atoms and molecules constituting it is emitted. The fluorescence is emitted from the specimen 53, the fluorescent marker, or the like in all directions, but in the configuration illustrated in FIG. 1, a component of the fluorescence emitted from the irradiation spot 72 in a specific direction (to the side) is fluorescence 74 to be analyzed. In addition, the light emitted from the irradiation spot 72 to the side includes side scattered light and the like in addition to the fluorescence, but in the following description, light components and the like other than the fluorescence 74 are appropriately omitted for simplification of description.

The forward scattered light 73 having passed through the irradiation spot 72 is converted into parallel light by the condenser lens 35 and is then incident on the photodiode 33 disposed at an angle slightly shifted from an optical axis on the side opposite to the excitation light source 32 with the irradiation spot 72 therebetween. On the other hand, the fluorescence 74 is converted into parallel light by the condenser lens 36 and is then incident on the spectral optical system 37. Note that each of the condenser lenses 35 and 36 may include another optical element such as a filter that absorbs a specific wavelength or a prism that changes a traveling direction of light. For example, the condenser lens 36 may include an optical filter that reduces the side scattered light in the incident side scattered light and fluorescence 74.

As illustrated in FIG. 2, the spectral optical system 37 is configured to include, for example, one or more optical elements 371 such as a prism and a diffraction grating, and disperses the incident fluorescence 74 into dispersed light 75 emitted at different angles for each wavelength. Note that, in the present description, a spreading direction H1 of the dispersed light 75, that is, a spectral direction by the spectral optical system 37 is defined as a row direction in a pixel array unit 91 of the image sensor 34 described later.

The dispersed light 75 emitted from the spectral optical system 37 is incident on the image sensor 34. Therefore, the dispersed light 75 having a different wavelength according to a position in a direction H1 is incident on the image sensor 34.

Here, while the forward scattered light 73 is light having a large amount of light, the side scattered light and the fluorescence 74 are weak pulsed light generated when the specimen 53 has passed through the irradiation spot 72. Therefore, in the present embodiment, the forward scattered light 73 is observed by the photodiode 33 to detect timing at which the specimen 53 has passed through the irradiation spot 72.

For example, the photodiode 33 constantly observes the forward scattered light 73 emitted from the irradiation spot 72. In this state, when the amount of light detected by the passage of the specimen 53 is increased by the forward scattered light 73, the photodiode 33 generates a trigger signal indicating the passage of the specimen 53 at timing when the amount of light has increased, and inputs the trigger signal to the image sensor 34.

The image sensor 34 is, for example, an imaging element including a plurality of pixels in which an analog to digital (AD) converter is built in the same semiconductor chip. Each pixel has a photoelectric conversion element and an amplification element, and the photoelectrically converted charge is accumulated inside the pixel. A signal (a pixel signal; also referred to as a pixel value) reflecting an accumulated charge amount is amplified and output via the amplification element at desired timing, and is converted into a digital signal by the built-in AD converter.

Note that, in the present description, although the so-called spectral type flow cytometer 11 that disperses the fluorescence 74 emitted from the specimen 53 by the wavelength has been exemplified, the present disclosure is not limited thereto, and may take a configuration where the fluorescence 74 is not dispersed, for example. In that case, the spectral optical system 37 may be omitted.

Further, in the present description, although the case where the forward scattered light 73 is used to generate the trigger signal has been exemplified, the present disclosure is not limited thereto, and the trigger signal may be generated using the side scattered light, the back scattered light, the fluorescence, or the like, for example.

2.2 Configuration Example of Image Sensor

Figure 3:
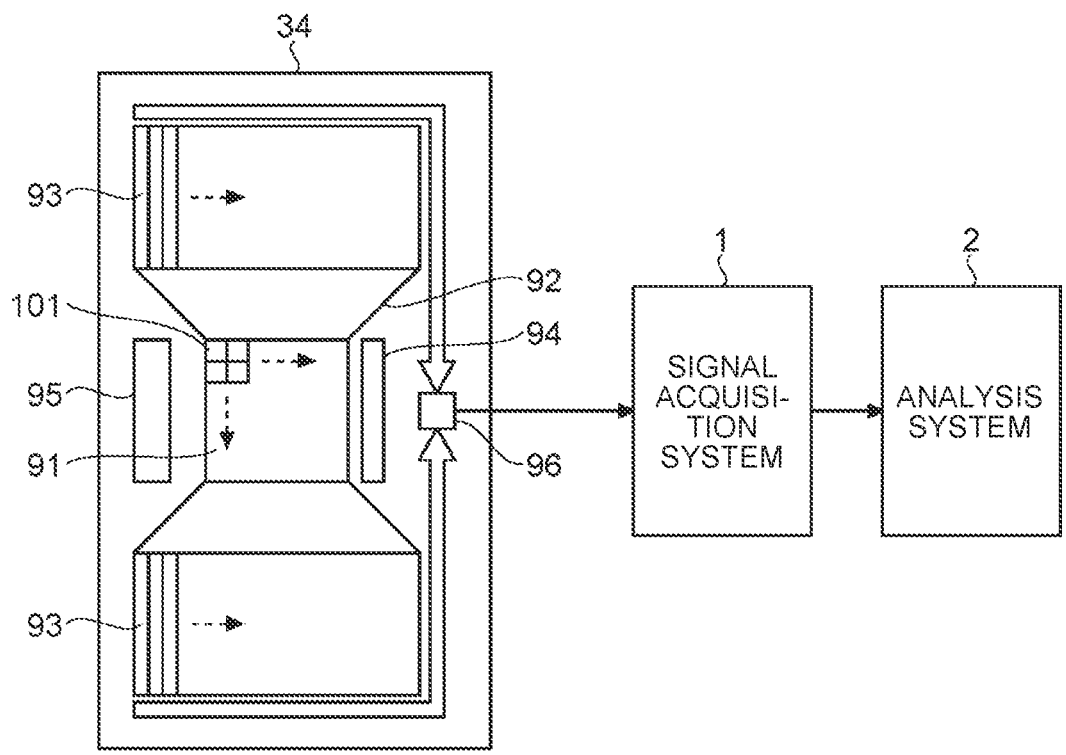
FIG. 3 is a block diagram illustrating a schematic configuration example of an image sensor according to the first embodiment.
Figure 4:
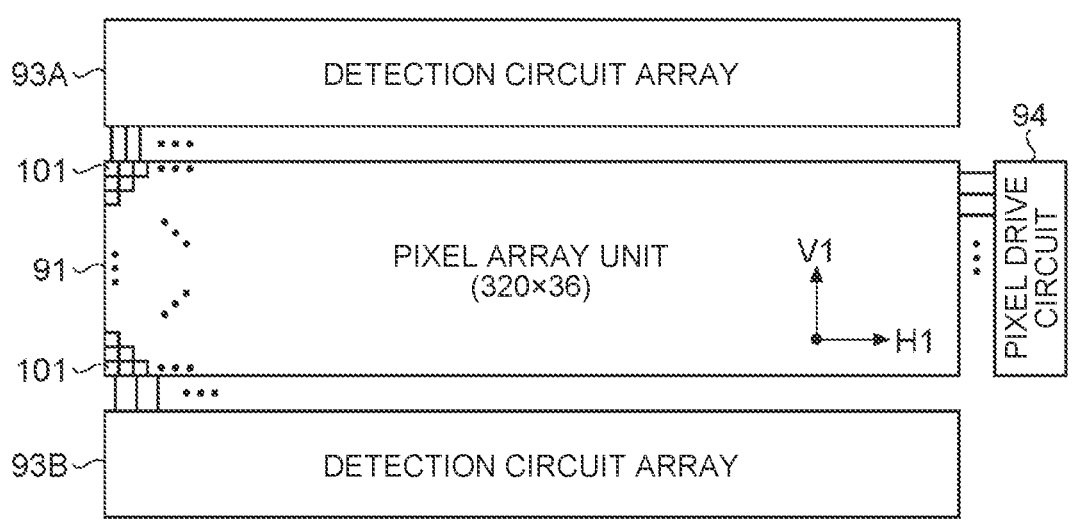
FIG. 4 is a diagram illustrating an example of a positional relation between a pixel array unit and a detection circuit array in FIG. 3.
Figure 5:
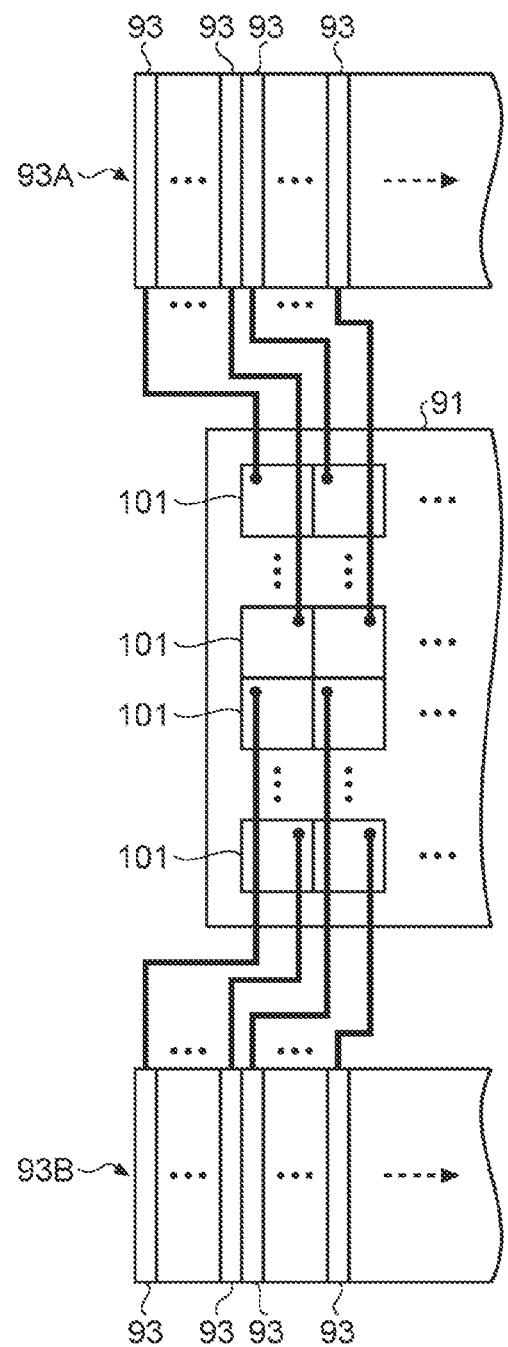
FIG. 5 is a diagram illustrating an example of a connection relation between a pixel and a detection circuit in FIG. 3.

Next, the image sensor 34 according to the first embodiment will be described. FIG. 3 is a block diagram illustrating a schematic configuration example of a complementary metal-oxide-semiconductor (CMOS) image sensor according to the first embodiment. FIG. 4 is a diagram illustrating an example of a positional relation between a pixel array unit and a detection circuit array in FIG. 3. FIG. 5 is a diagram illustrating an example of a connection relation between a pixel and a detection circuit in FIG. 3.

Here, the CMOS image sensor is a solid-state imaging element (also referred to as a solid-state imaging device) created by applying or partially using a CMOS process. The image sensor 34 according to the first embodiment may be of a so-called back surface irradiation type in which an incident surface is a surface (hereinafter, referred to as a back surface) on the side opposite to an element forming surface in a semiconductor substrate, or may be of a so-called front surface irradiation type in which the incident surface is a front surface. Note that the size, the number, the number of rows, the number of columns, and the like exemplified in the following description are merely examples, and can be variously changed.

As illustrated in FIG. 3, the image sensor 34 includes a pixel array unit 91, a connection unit 92, a detection circuit 93, a pixel drive circuit 94, a logic circuit 95, and an output circuit 96.

The pixel array unit 91 includes, for example, a plurality of pixels 101 arranged in a matrix (hereinafter, referred to as 320×36 pixels) of 320 pixels in a row direction H1 and 36 pixels in a column direction V1. A size of each pixel 101 on an array surface may be, for example, 15 μm (micrometers)× 15 μm. In this case, an opening of the pixel array unit 91 is 4.8 mm (millimeters)×0.54 mm.

The pixel drive circuit 94 drives each pixel 101 to cause each pixel 101 to generate a pixel signal. The logic circuit 95 controls drive timing of the detection circuit 93 or the output circuit 96 in addition to the pixel drive circuit 94. Further, the logic circuit 95 and/or the pixel drive circuit 94 also functions as a control unit that controls reading of the pixel signal with respect to the pixel array unit 91 in accordance with the passage of the irradiation spot 72 by the specimen 53.

Note that the image sensor 34 may further include an amplifier circuit such as an operational amplifier that amplifies a pixel signal before AD conversion.

The fluorescence 74 emitted from the irradiation spot 72 to the side is collimated by the condenser lens 36 and then converted into the dispersed light 75 by the spectral optical system 37. Then, the dispersed light 75 is incident on a different region on a light receiving surface on which the pixels 101 of the pixel array unit 91 are arranged.

A wavelength component determined by a position of the row direction H1 in the pixel array unit 91 in the dispersed light 75 is input to each pixel 101 of the pixel array unit 91. For example, in the positional relation illustrated in FIG. 2, light having a shorter wavelength is incident on the pixel 101 located on the right side in the image sensor 34 of FIG. 2, and light having a longer wavelength is incident on the pixel 101 located on the left side.

Each pixel 101 generates a pixel signal according to a light irradiation amount. The generated pixel signal is read by, for example, the detection circuit 93 provided on a one-to-one basis with respect to the pixel 101. Each detection circuit 93 includes an AD converter, and converts the read analog pixel signal into a digital pixel signal.

Here, as illustrated in FIGS. 4 and 5, a plurality of detection circuits 93 are arranged to be divided into two groups (detection circuit arrays 93A and 93B) with respect to the pixel array unit 91, for example. One detection circuit array 93A is disposed, for example, above the pixel array unit 91 in the column direction, and the other detection circuit array 93B is disposed, for example, below the pixel array unit 91 in the column direction. In each of the detection circuit arrays 93A and 93B, the plurality of detection circuits 93 are arranged in one row or a plurality of rows along the row direction.

For example, each detection circuit 93 of the detection circuit array 93A disposed above the pixel array unit 91 in the column direction may be connected to the pixels 101 in the upper half of the pixel array unit 91 in the column direction, and each detection circuit 93 of the detection circuit array 93B disposed below the pixel array unit 91 in the column direction may be connected to the pixels 101 in the lower half of the pixel array unit 91 in the column direction. However, the present disclosure is not limited thereto, and various modifications may be made, for example, each detection circuit 93 of the detection circuit array 93A may be connected to the pixels 101 of even-numbered columns, and each detection circuit 93 of the detection circuit array 93B may be connected to the pixels 101 of odd-numbered columns. Further, for example, the plurality of detection circuits 93 may be arranged in one row or a plurality of rows on one side (for example, the upper side in the column direction) of the pixel array unit 91.

In the pixel array unit 91, 36 pixels 101 are arranged in the column direction V1. For this reason, it is necessary to dispose 36 detection circuits 93 for one column of pixels. Therefore, as described above, in a case where the detection circuits 93 are grouped into the two detection circuit arrays 93A and 93B and the number of rows thereof is set to one row, for 36 pixels 101 arranged in one column, 18 detection circuits 93 may be disposed in each of the detection circuit arrays 93A and 93B.

The description returns to FIG. 3. The pixel signal read from each pixel 101 by the detection circuit 93 is converted into a digital pixel signal by an AD converter of each detection circuit 93. In addition, the digital pixel signal is output as fluorescence information (corresponding to fluorescence spectrum information; hereinafter, referred to as a spectral image) indicating information for each wavelength of the fluorescence 74 to an external signal acquisition system 1 via the output circuit 96.

For example, the signal acquisition system (also referred to as a signal acquisition unit) 1 evaluates the spectral image input from the image sensor 34, and inputs an evaluation value as a result to an analysis system 2. For example, the signal acquisition system 1 divides the spectral image into a plurality of regions (corresponding to channel regions to be described later) arranged along the row direction H1, and adds pixel values of pixels included in the respective regions, thereby calculating an evaluation value of the spectral image (corresponding to multichannel analysis to be described later). Further, the signal acquisition system 1 may have a so-called virtual filter function of calculating an evaluation value of a spectral image by adding pixel values of pixels included in each of one or more regions (corresponding to a virtual filter to be described later) set in advance or arbitrarily set by the user.

The signal acquisition system 1 may be a digital signal processor (DSP), a field-programmable gate array (FPGA), or the like provided in the same chip as or outside the image sensor 34, or may be an information processing device such as a personal computer connected to the image sensor 34 via a bus or a network.

The analysis system (also referred to as an analysis unit) 2 executes various analysis processing on the basis of the evaluation value input from the signal acquisition system 1. For example, the analysis system 2 acquires information such as a type, a size, and a structure of the specimen 53 on the basis of the evaluation value. Further, the analysis system 2 may display the spectral image or the evaluation value to the user and provide a user interface (UI) to be an analysis tool. The analysis system 2 may be, for example, an information processing device such as a personal computer connected to the signal acquisition system 1 via a bus or a network.

2.3 Circuit Configuration Example of Pixel

Figure 6:
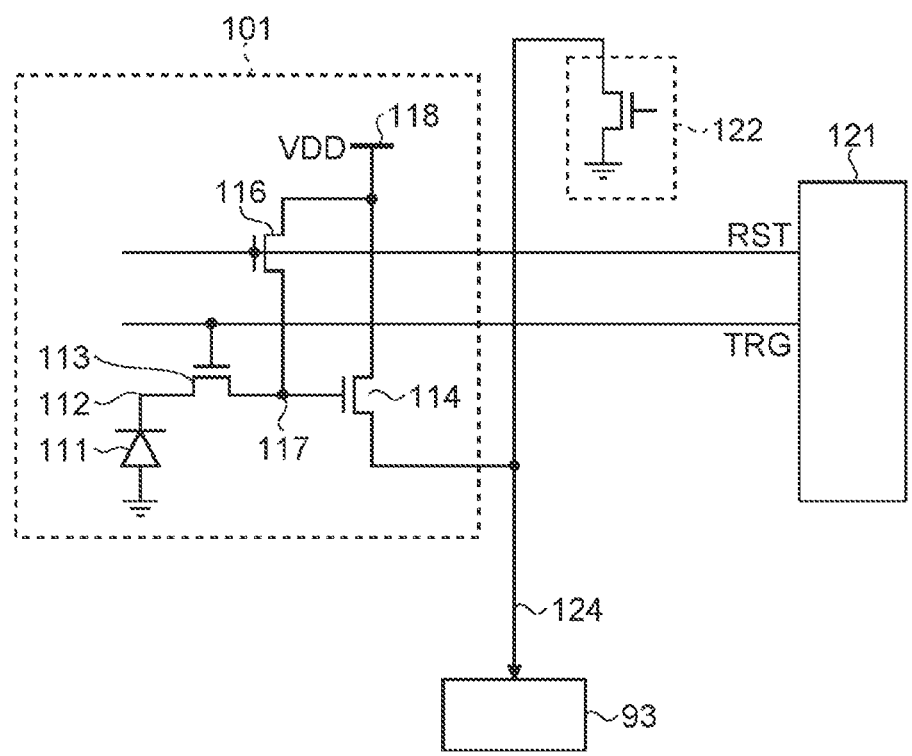
FIG. 6 is a circuit diagram illustrating a circuit configuration example of a pixel according to the first embodiment.

Next, a circuit configuration example of the pixel 101 according to the first embodiment will be described with reference to FIG. 6. FIG. 6 is a circuit diagram illustrating a circuit configuration example of the pixel according to the first embodiment.

As illustrated in FIG. 6, the pixel 101 includes a photodiode (also referred to as a photoelectric conversion element) 111, an accumulation node 112, a transfer transistor 113, an amplification transistor 114, a reset transistor 116, and a floating diffusion (FD) layer 117. For example, an N-type metal-oxide-semiconductor (MOS) transistor may be used for the transfer transistor 113, the amplification transistor 114, and the reset transistor 116.

A circuit including the photodiode 111, the transfer transistor 113, the amplification transistor 114, the reset transistor 116, and the floating diffusion layer 117 is also referred to as a pixel circuit. Further, a configuration of the pixel circuit excluding the photodiode 111 is also referred to as a read circuit.

The photodiode 111 converts photons into charges by photoelectric conversion. The photodiode 111 is connected to the transfer transistor 113 via the accumulation node 112. The photodiode 111 generates a pair of an electron and a hole from a photon incident on the semiconductor substrate on which the photodiode is formed, and accumulates the electron in the accumulation node 112 corresponding to a cathode. The photodiode 111 may be of a so-called embedded type in which the accumulation node 112 is completely depleted at the time of charge discharge by resetting.

The transfer transistor 113 transfers the charge from the accumulation node 112 to the floating diffusion layer 117 under the control of a row drive circuit 121. The floating diffusion layer 117 accumulates the charge from the transfer transistor 113 and generates a voltage of a voltage value according to the amount of accumulated charge. This voltage is applied to a gate of the amplification transistor 114.

The reset transistor 116 releases the charges accumulated in the accumulation node 112 or the floating diffusion layer 117 to a power supply 118 and performs initialization. A gate of the reset transistor 116 is connected to the row drive circuit 121, a drain thereof is connected to the power supply 118, and a source thereof is connected to the floating diffusion layer 117.

For example, the row drive circuit 121 controls the reset transistor 116 and the transfer transistor 113 to be in an on state, thereby extracting the electrons accumulated in the accumulation node 112 to the power supply 118 and initializing the pixel 101 to a dark state before accumulation, that is, a state in which light is not incident. Further, the row drive circuit 121 controls only the reset transistor 116 to be in the on state, thereby extracting the charges accumulated in the floating diffusion layer 117 to the power supply 118 and initializing the charge amount.

The amplification transistor 114 amplifies the voltage applied to the gate and causes the voltage to appear at the drain. A gate of the amplification transistor 114 is connected to the floating diffusion layer 117, a source thereof is connected to the power supply, and a drain thereof is connected to a vertical signal line 124.

The amplification transistor 114 and a constant current circuit 122 form a source follower circuit. The amplification transistor 114 amplifies the voltage of the floating diffusion layer 117 with a gain of less than 1 and causes the voltage to appear in the vertical signal line 124. The voltage appearing in the vertical signal line 124 is read as a pixel signal by the detection circuit 93 including an AD conversion circuit.

The pixel 101 having the above configuration internally accumulates the charge generated by the photoelectric conversion during a period from when resetting of the photodiode 111 is executed to when reading of the pixel signal is executed. When reading of the pixel signal is executed, the pixel signal according to the accumulated charge is caused to appear in the vertical signal line 124.

Note that the row drive circuit 121 in FIG. 6 may be, for example, a part of the pixel drive circuit 94 in FIG. 3, and the detection circuit 93 and the constant current circuit 122 may be, for example, a part of the detection circuit 93 in FIG. 3.

2.4 Operation Example of Pixel

Figure 7:
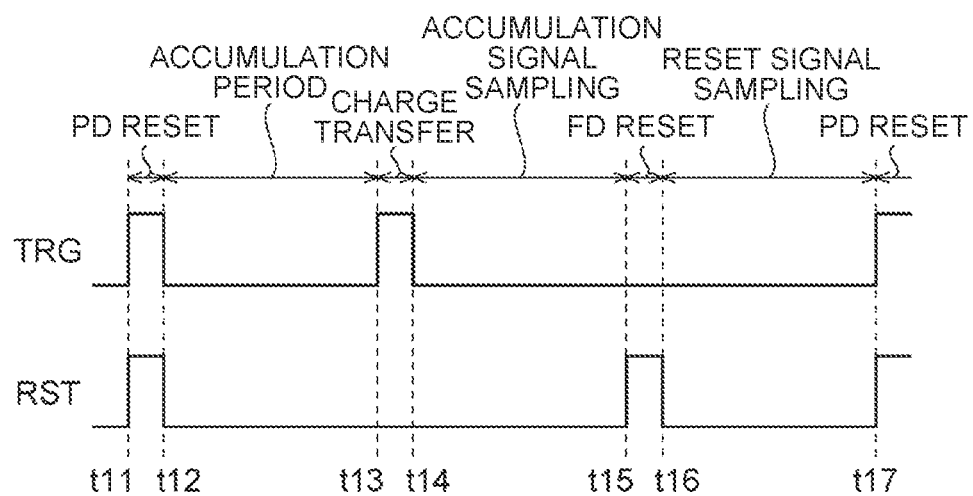
FIG. 7 is a timing chart illustrating an operation example of the pixel according to the first embodiment.

Next, an operation example of the pixel 101 according to the first embodiment will be described with reference to a timing chart of FIG. 7. FIG. 7 is a timing chart illustrating an operation example of the pixel according to the first embodiment.

As illustrated in FIG. 7, at timings t11 to t12, the row drive circuit 121 raises a transfer control signal TRG to be applied to the gate of the transfer transistor 113 and a reset control signal RST to be applied to the gate of the reset transistor 116 to a high level at timing immediately before an accumulation period. As a result, both the transfer transistor 113 and the reset transistor 116 are turned on, and the charge accumulated in the accumulation node 112 between the photodiode 111 and the transfer transistor 113 is discharged to the power supply 118. Hereinafter, this control is referred to as "PD reset".

Further, in a case where the reset transistor 116 is turned on, since the floating diffusion layer 117 is also connected to the power supply 118 via the reset transistor 116, the charge accumulated in the floating diffusion layer 117 is also discharged to the power supply 118.

At timing t12, the row drive circuit 121 lowers the transfer control signal TRG and the reset control signal RST to a low level, thereby controlling the transfer transistor 113 and the reset transistor 116 to be in an off-state. With this control, the accumulation node 112 enters a floating state, and a new accumulation period is started.

Next, at timings t13 to t14, the row drive circuit 121 raises the transfer control signal TRG to a high level. As a result, the transfer transistor 113 is turned on, and the charge accumulated in the accumulation node 112 between the photodiode 111 and the transfer transistor 113 is transferred to the floating diffusion layer 117. Hereinafter, this control is referred to as "charge transfer".

As described above, when the charge generated in the photodiode 111 is transferred to the floating diffusion layer 117, a voltage of a voltage value according to the charge amount of the charge accumulated in the floating diffusion layer 117 is amplified by the amplification transistor 114 and appears in the vertical signal line 124. In the present description, a potential appearing in the vertical signal line 124 in a state where the charge generated in the photodiode 111 is accumulated in the floating diffusion layer 117 is referred to as an accumulation signal.

The detection circuit 93 performs signal reading (hereinafter, referred to as sampling) of the accumulation signal appearing in the vertical signal line 124 during a period from timing t14 to timing t15 when the transfer control signal TRG falls to a low level. In this sampling, the accumulation signal appearing in the vertical signal line 124 is read by the detection circuit 93 as a pixel signal of a voltage value according to the exposure amount to the photodiode 111, and is converted into a digital signal. The multiple sampling of the accumulation signal is handled as first read in correlated double sampling (CDS) described later.

Next, at timings t15 to t16, the row drive circuit 121 raises the reset control signal RST to a high level. As a result, the reset transistor 116 is turned on, and the charge accumulated in the floating diffusion layer 117 is discharged to a power supply line VDD via the reset transistor 116. Hereinafter, this control is referred to as "FD reset".

As described above, when the floating diffusion layer 117 is reset, the voltage of the floating diffusion layer 117 in a reset state is amplified by the amplification transistor 114 and appears in the vertical signal line 124. In the present description, the potential appearing in the vertical signal line 124 when the floating diffusion layer 117 is in a reset state is referred to as a reset level.

Similarly to the sampling of the accumulation signal, the detection circuit 93 samples a pixel signal of a reset level appearing in the vertical signal line 124 during a period from timing t16 to timing t17 when the reset control signal RST falls to a low level. In this sampling, the reset level appearing in the vertical signal line 124 is read by the detection circuit 93 as a pixel signal of a voltage value (reset level) when the floating diffusion layer 117 is in a reset state, and is converted into a digital signal. This multiple sampling of the reset level is handled as second read in correlated double sampling (CDS) described later.

The detection circuit 93 compares the sampled accumulation signal with the reset signal, and determines an incident photon amount on the basis of a comparison result.

Note that the detection circuit 93 may perform sampling of the accumulation signal a plurality of times, add all values, and calculate an average value thereof as necessary. Similarly, the detection circuit 93 may perform sampling of the reset signal a plurality of times, add all values, and calculate an average value thereof as necessary.

Then, the detection circuit 93 executes CDS for calculating a difference between the accumulation signal (or the average value thereof) and the reset signal (or the average value thereof). By the CDS, kTC noise occurring at the time of the FD reset is canceled, and a net pixel signal based on the light amount of the fluorescence 74 is obtained.

The accumulation period of each pixel (pixel circuit) 101 is a period between the PD reset operation and the accumulation signal read operation described above, and to be precise, the accumulation period is a period from when the transfer control signal TRG falls at the time of the PD reset to when the transfer control signal TRG falls again at the time of the charge transfer. During the accumulation period, when photons are incident on the photodiode 111 and charges are generated, this is a difference between the reset signal and the accumulation signal, and is acquired by the detection circuit 93 as the net pixel signal.

Note that, in the detection circuit 93, by performing the CDS between the digital values through the AD converter, noise mixed during the AD conversion process can also be canceled.

2.4.1 Modification of Pixel Operation

Incidentally, in the operation example using FIG. 7, a dead period in which the accumulation is not performed occurs while the unit accumulation is completed and the next accumulation is started, particularly, in the sampling period of the accumulation signal. Therefore, in particular, in order to cope with high-speed sampling, the dead period may be removed.

Figure 8:
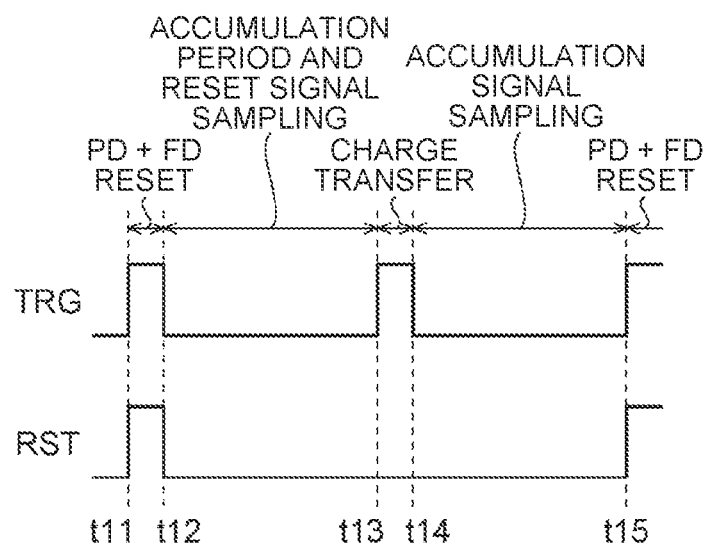
FIG. 8 is a timing chart illustrating an operation example of a pixel according to a modification of the first embodiment.

FIG. 8 is a timing chart illustrating an operation example of a pixel according to a modification. In the example of FIG. 8, the FD reset at the timings t15 to t16 performed in FIG. 7 is omitted, and the sampling of the reset signal is executed during the accumulation period of the timings t12 to t13 after the PD reset.

In this case, a next accumulation period of the photodiode 111 starts immediately after the charge transfer is completed, that is, when the transfer control signal TRG is lowered. As a result, the dead period during which no photon incident on the pixel 101 is detected is almost zero.

Note that, in both the operation examples of FIGS. 7 and 8, a shortest cycle of the unit accumulation can be defined by a total required time of the sampling of the reset signal and the sampling of the accumulation signal.

2.5 Operation Example of Pulsed Light Detection

Figure 9:
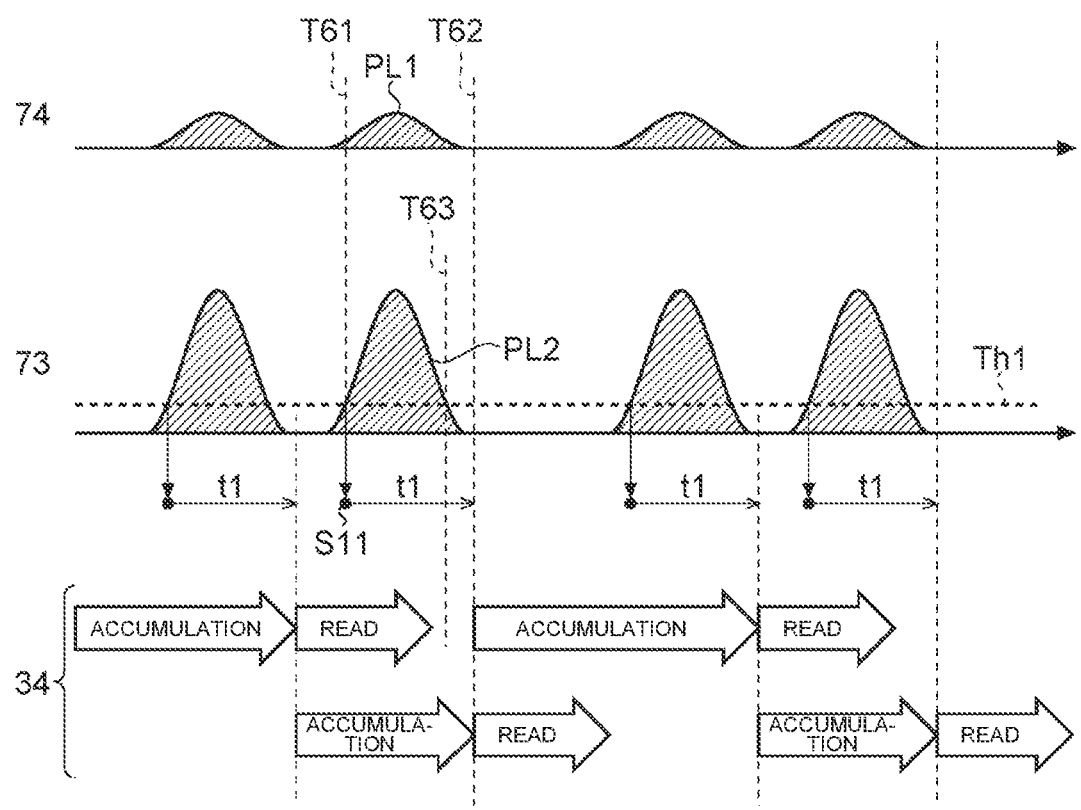
FIG. 9 is a timing chart for explaining an operation example of pulsed light detection in the flow cytometer according to the first embodiment.

Next, an operation example of pulsed light detection in the flow cytometer 11 according to the first embodiment will be described with reference to the timing chart of FIG. 9. FIG. 9 is a timing chart for explaining an operation example of the pulsed light detection in the flow cytometer according to the first embodiment.

The light intensity of the fluorescence 74 is drawn as a pulse waveform PL1 as illustrated in the uppermost part of FIG. 9 as the specimen 53 passes through the irradiation spot 72, and each pulse waveform PL1 becomes a waveform corresponding to the passage of one specimen 53. At this time, the light intensity of the forward scattered light 73 detected by the photodiode 33 illustrated in the middle part of FIG. 9 is drawn as a pulse waveform PL2 having timing similar to timing of the pulse waveform PL1 in the upper part of FIG. 9 and a high intensity increase rate.

At timing T61, the photodiode 33 acquires passage timing of the specimen 53 from a comparison between the intensity of the pulse waveform PL2 of the forward scattered light and a threshold Th1, and generates an event signal S11.

Here, the end of the accumulation period and the signal read in the image sensor 34 are performed in synchronization with the event signal S11 indicating that the passage of the specimen 53. It is assumed that a read access sequence is a global shutter with almost no dead period according to FIG. 9.

That is, the start and end of the accumulation period are performed simultaneously for all the pixels. At this time, in-pixel transfer of charges is performed in synchronization with the event signal S11 indicating the passage of the specimen 53, and the accumulation period ends simultaneously for all the pixels. Then, reading of the pixel signal is started. Furthermore, at this time, a next accumulation period starts simultaneously for all the pixels.

At timing T62, the image sensor 34 ends the accumulation period in the pixel, starts reading of the pixel signal, and further starts a next accumulation period. Here, the timing T62 is timing after a certain delay time t1 considering the flow velocity and magnitude of the specimen 53 elapses from the timing T61 when the event signal S11 is acquired.

The reading of the pixel signal is performed with acquisition of a difference between the AD conversion value of the accumulation signal and the AD conversion value of the reset signal that has already been acquired, thereby deriving a net pixel signal in which kTC noise or the like has been canceled. Further, subsequently, the acquisition of the reset signal and the AD conversion in a next cycle are performed, and when the acquisition and the AD conversion are completed, the end and the read of a next accumulation period are enabled. That is, a shortest cycle of the event processing is equal to a shortest cycle of the unit accumulation period, which is determined by a time required for acquisition and AD conversion of each of the accumulation signal and the reset signal.

A total value of the net pixel signals output from the plurality of pixels 101 in each event processing corresponds to a total amount of photons received by the photodetector for each pulse. As a result, the intensity of the fluorescence 74 for each specimen 53 is derived. That is, in the present embodiment, the pixel 101 internally accumulates the photoelectrically converted charge, so that the incident light is integrated in the pixel 101. Therefore, the AD conversion for the output from each pixel 101 may be performed once, and it is not necessary to perform the AD conversion a plurality of times in time series.

For example, when it is assumed that a total time of 10 μs is required for the AD conversion of the reset signal, the AD conversion of the accumulation signal, and the CDS thereof, a minimum interval of events that can be handled is about 10 μs, and a maximum of 100,000 events in one second, that is, the passage of the specimen 53 to the irradiation spot 72 can be evaluated.

In addition to the time for reading the pixel signal from each pixel 101, a time for outputting the pixel signal read via the output circuit 96 is also required. However, for example, by providing a register in the detection circuit 93 and temporarily storing the pixel signal, the AD conversion of the reset signal and the accumulation signal and the output of the pixel signal can be executed in parallel in a pipeline system. Therefore, the time required for outputting the pixel signal does not restrict the accumulation cycle.

Further, in this example, the event signal S11 indicating the passage of the specimen 53 is generated at the down edge timing T61 when the pulse waveform PL2 falls below the threshold L1. However, the present disclosure is not limited thereto, and the event signal S11 may be generated at up edge timing T63 when the pulse waveform PL2 exceeds the threshold L1. When the event signal S11 is generated at the up edge timing T63, it is easy to cope with a variation in the size or the flow rate of the specimen 53.

Further, the event signal S11 may be generated using the detection result of the side scattered light or the fluorescence 74 (dispersed light 75). In that case, the light for event detection and the light for specimen analysis may be dispersed, and the light for event detection may be caused to be incident on the photodiode 33.

Further, instead of the photodiode 33, a light receiving element for event generation may be separately mounted in the image sensor 34.

Furthermore, although the delay time t1 from the event signal S11 is constant here, in general, the intensity attenuation amount of the pulse waveform PL2 due to the forward scattered light 73 is larger as the specimen 53 is larger. Therefore, the intensity of the pulse waveform PL2 may be evaluated, for example, at the beginning of the pulse, and the length of the delay time t1 may be set accordingly. In this case, the long delay time t1 may be set for the large specimen 53.

Furthermore, in the present description, a so-called global shutter system in which read is simultaneously started for all the pixels of the pixel array unit 91 has been exemplified, but the present disclosure is not limited thereto. For example, in a case where one detection circuit 93 is connected to a plurality of pixels 101 in the same column, it is also possible to adopt a so-called rolling shutter system in which pixel signals are sequentially read from the pixels 101 connected to the same detection circuit 93. Note that, in a case where the rolling shutter system is adopted, a selection transistor that controls connection between the drain of the amplification transistor 114 and the vertical signal line 124 according to a selection signal from the row drive circuit 121 is added to the drain of the amplification transistor 114 and the vertical signal line 124 in the pixel circuit of each pixel 101.

Figure 10:
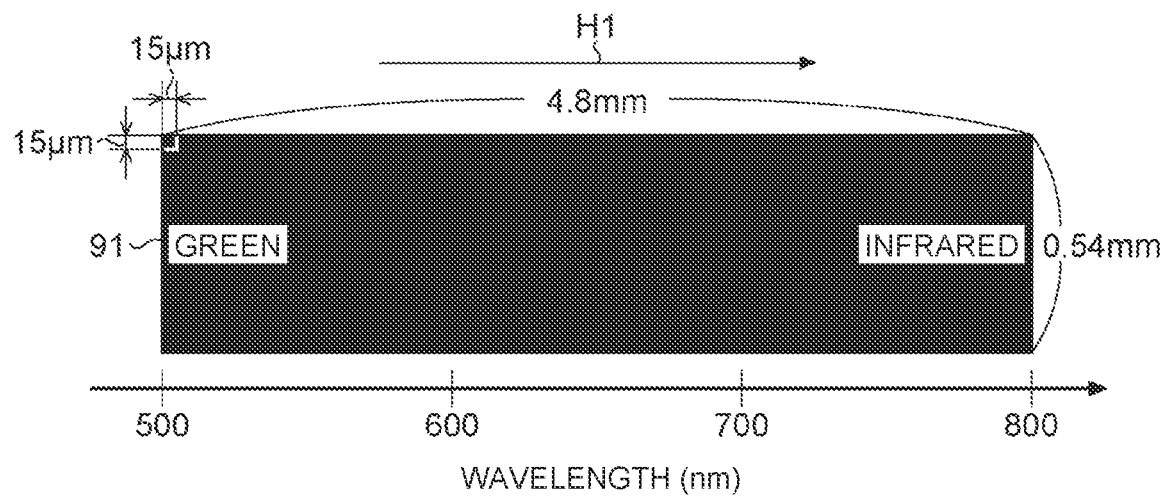
FIG. 10 is a diagram illustrating an example of a relation between a position on the pixel array unit and a wavelength of dispersed light in the first embodiment.

2.6 Example of Relation Between Position on Pixel Array Unit and Wavelength of Dispersed Light FIG. 10 is a diagram illustrating an example of a relation between the position on the pixel array unit and the wavelength of the dispersed light in the first embodiment. As described above, the spectral optical system 37 disperses the fluorescence 74 in the row direction H1 and emits the dispersed light 75 spreading in the row direction H1. In the example illustrated in FIG. 10, the spectral optical system 37 disperses the fluorescence 74 such that light having a wavelength of 500 nm is incident on the pixel 101 located on the leftmost side in the row direction H1 and light having a wavelength of 800 nm is incident on the pixel 101 located on the rightmost side. Here, as described above, when it is assumed that the number of pixels in the row direction H1 in the pixel array unit 91 is 320, light having a wavelength width of about 0.9 to 1 nm is incident on each pixel 101 according to the position in the row direction H1.

2.7 Case where Image Sensor is Multichannelized

Figure 11:
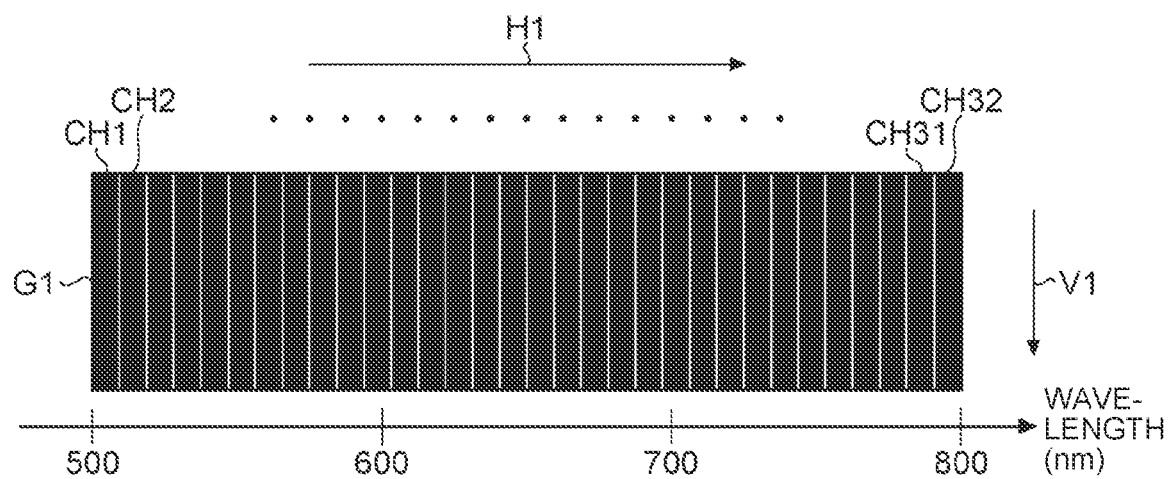
FIG. 11 is a diagram illustrating an example of a case where the image sensor according to the first embodiment is multichannelized.

FIG. 11 is a diagram illustrating an example of a case where the image sensor according to the first embodiment is multichannelized. That is, in the present description, a case where the image sensor 34 is used as a multichannel PMT is exemplified. Note that FIG. 11 illustrates a case where the image sensor 34 is divided into 32 channels.

As illustrated in FIG. 11, in a case where the image sensor 34 is multichannelized with 32 channels, the pixel array unit 91 is divided into a total of 32 regions each having 10 pixels in the row direction H1. Specifically, the signal acquisition system 1 divides the spectral image G1 acquired from the pixel array unit 91 into a total of 32 channel regions CH1 to CH32 each having 10 pixels in the row direction H1. In this case, the wavelength width of the light included in each of the channel regions CH1 to CH32 is about 9 to 10 nm.

Note that the number of channels realized in the multichannel conversion, that is, the number of divisions in the row direction H1 of the pixel array unit 91 or the spectral image G1 is not limited to 32, and can be variously modified. For example, in a case where the number of pixels in the row direction H1 in the pixel array unit 91 is 320, the pixel array unit can be divided into channel regions of at least 1 channel and at most 320 channels.

Further, in the present embodiment using the image sensor 34 as a light detection unit, for example, the width (the number of pixels) of each channel region in the row direction H1 can be separately set for each channel region.

For example, in a case where a prism is used for the spectral optical system 37, light having a long wavelength spreads in the row direction H1 more widely than light having a short wavelength. In such a case, for example, in the example illustrated in FIG. 11, the number of pixels in the row direction H1 of the channel regions CH31, CH32, and the like on which light having a long wavelength is incident may be larger than the number of pixels in the row direction H1 of the channel regions CH1, CH2, and the like on which light having a short wavelength is incident. That is, when the spectral optical system 37 includes a prism that disperses the fluorescence 74 in a predetermined direction (for example, a direction corresponding to the row direction H1), the width (number of pixels) in the row direction H1 of the first region (for example, the channel region CH1) on which the first wavelength component of the fluorescence 74 is incident may be smaller than the width (number of pixels) in the row direction H1 of the second region (for example, the channel region CH32) on which the second wavelength component longer than the first wavelength component is incident.

As described above, in the present embodiment, when the multichannel analysis is performed on the fluorescence 74, the number of channels, the channel width (wavelength width) of each channel, the center wavelength of each channel, and the like can be freely designed.

2.8 Case where Virtual Filter Function is Realized by Image Sensor

Figure 12:
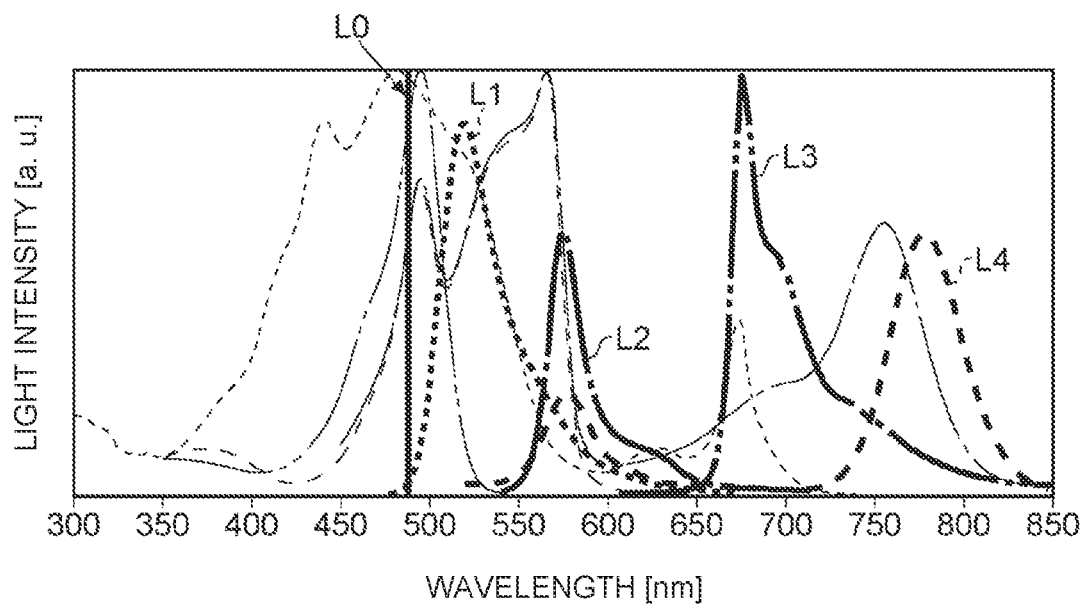
FIG. 12 is a diagram illustrating spectra of fluorescence emitted from four types of fluorescent dyes excited by excitation light having a wavelength of 488 nm.
Figure 13:
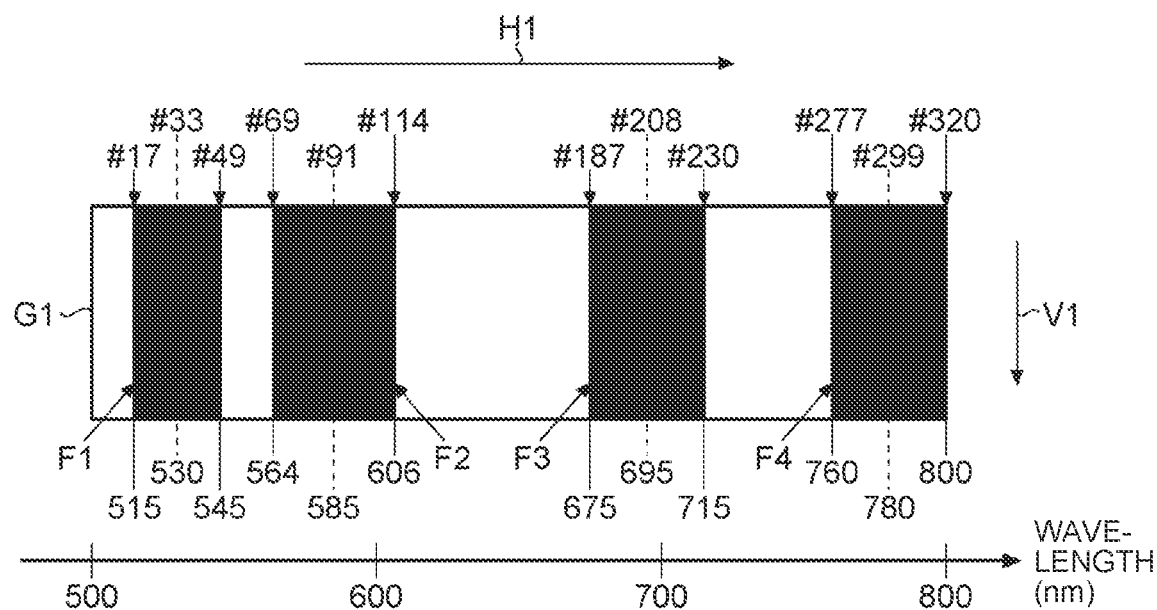
FIG. 13 is a diagram illustrating an example of a virtual filter according to the first embodiment realized for the fluorescence illustrated in FIG. 12.

Further, a virtual filter function can be realized using the image sensor 34 according to the present embodiment. FIG. 12 is a diagram illustrating spectra of fluorescence emitted from four types of fluorescent dyes including FITC, PE, PerCP-Cy5.5, and PE-Cy7, excited by excitation light with a wavelength of 488 nm. FIG. 13 is a diagram illustrating an example of a virtual filter according to the first embodiment realized for the fluorescence illustrated in FIG. 12. Note that, in FIG. 13, a pixel column of a left end in the pixel array unit 91 is a pixel column #1, and a pixel column of a right end is a pixel column #320.

As illustrated in FIG. 12, when four types of fluorescent dyes including FITC, PE, PerCP-Cy5.5, and PE-Cy7, are irradiated with excitation light L0 of 488 nm, fluorescence L1 having a center wavelength of about 530 nm is emitted from FITC, fluorescence L2 having a center wavelength of about 585 is emitted from PE, fluorescence L3 having a center wavelength of about 695 nm is emitted from PerCP-Cy5.5, and fluorescence L4 having a center wavelength of about 780 nm is emitted from PE-Cy7.

Therefore, as illustrated in FIG. 13, for the fluorescence L1 from FITC, the signal acquisition system 1 sets a virtual filter (also referred to as a filter region) F1 in which the center in the row direction H1 is a pixel column #33 corresponding to a wavelength of 530 nm and the width in the row direction H1 is 33 pixels corresponding to a wavelength of 30 nm, in the spectral image G1. For the fluorescence L2 from PE, a virtual filter F2 in which the center in the row direction H1 is a pixel column #91 corresponding to a wavelength of 585 nm and the width in the row direction H1 is 46 pixels corresponding to a wavelength of 42 nm is set in the spectral image G1. For the fluorescence L3 from PerCP-Cy5.5, a virtual filter F3 in which the center in the row direction H1 is a pixel column #208 corresponding to a wavelength of 695 nm and the width in the row direction H1 is 44 pixels corresponding to a wavelength of 40 nm is set in the spectral image G1. For the fluorescence L4 from PE-Cy7, a virtual filter F4 in which the center in the row direction H1 is a pixel column #299 corresponding to a wavelength of 780 nm and the width in the row direction H1 is 44 pixels corresponding to a wavelength of 40 nm is set in the spectral image G1.

Note that, in each of the virtual filters F1 to F4, the number of pixels in the column direction V1 may be, for example, 36 pixels, which is the same as the number of pixels in the column direction V1 of the pixel array unit 91.

In a case where the virtual filters F1 to F4 described above are set to the spectral image G1, from the signal acquisition system 1, for example, a sum of the pixel signals output from the respective pixels 101 of 33×36 pixels constituting the virtual filter F1, a sum of the pixel signals output from the respective pixels 101 of 46×36 pixels constituting the virtual filter F2, a sum of the pixel signals output from the respective pixels 101 of 44×36 pixels constituting the virtual filter F3, and a sum of the pixel signals output from the respective pixels 101 of 44×36 pixels constituting the virtual filter F4 is output as an evaluation value.

As described above, in the present embodiment, by using the image sensor 34 as the photodetector, it is possible to acquire fluorescence spectrum information with fine wavelength resolution and high resolution. Therefore, it is possible to improve the reproducibility of optical filter characteristics and to set an optimal virtual filter for fluorescence emitted from each fluorescent dye.

Note that the number of virtual filters to be set, the center wavelength and/or the wavelength width of each virtual filter, and the like can be freely designed according to the wavelength of the excitation light 71 to be used, the type of the specimen 53 and/or the fluorescent marker, and the like. For example, in a case where another fluorescent dye is added to the four fluorescent dyes illustrated in FIG. 12, it is possible to set a virtual filter corresponding to the added fluorescent dye in the spectral image G1. At that time, in a region where different fluorescence spectra are close to each other, the center wavelength and/or the wavelength width of each virtual filter may be adjusted.

Further, in a case where a multispot type flow cytometer is used, it is also possible to set an optimal virtual filter according to fluorescence emitted from the specimen 53 and/or the fluorescent marker by each excitation light 71.

2.9 Function and Effect

As described above, according to the first embodiment, in the spectral type flow cytometer 11, the two-dimensional image sensor 34 is used in the array type photodetector. For this reason, the device scale can be downsized as compared with a case where the multichannel PMT is used in the array type photodetector. As a result, the overall device scale can be reduced.

Furthermore, since the image sensor 34 can acquire fluorescence spectrum information having finer wavelength resolution and higher resolution than the multichannel PMT, it is possible to realize a virtual filter that faithfully reproduces optical filter characteristics.

Furthermore, since it is possible to add pixel values at an arbitrary wavelength width by using the image sensor 34, there is also an advantage that it is easy to change the design after productization, such as an increase or decrease in the number of channels or a change in the channel width when multichannel analysis is performed, an increase or decrease in the number of filters when a virtual filter function is used, or a change in the center wavelength/wavelength width of each filter.

3. SECOND EMBODIMENT

In the first embodiment described above, a spectral type flow cytometer has been exemplified, but the technology according to the present disclosure is not limited to the flow cytometer, and can be applied to, for example, a medical device such as digital pathology imaging (DPI).

In the digital pathology imaging (DPI), a specimen 53 is placed on a stage, and the specimen 53 placed on the stage is scanned by excitation light 71 from an excitation light source 32. Scanning of the specimen 53 placed on the stage by the excitation light 71 is controlled by a scanning control unit that controls a positional relation between the stage and the excitation light source 32.

Further, in the digital pathology imaging (DPI), a line sensor in which pixels 101 are linearly arranged is used as an image sensor 34. The line sensor receives fluorescence 74 emitted from the specimen 53 when the excitation light 71 scans the specimen 53 on the stage, and generates two-dimensional or three-dimensional image data (spectral image) of the entire specimen 53.

Similarly to the first embodiment, the generated spectral image is input to a signal acquisition system 1 and evaluated, and an evaluation value is input to an analysis system 2 and analyzed.

Figure 14:
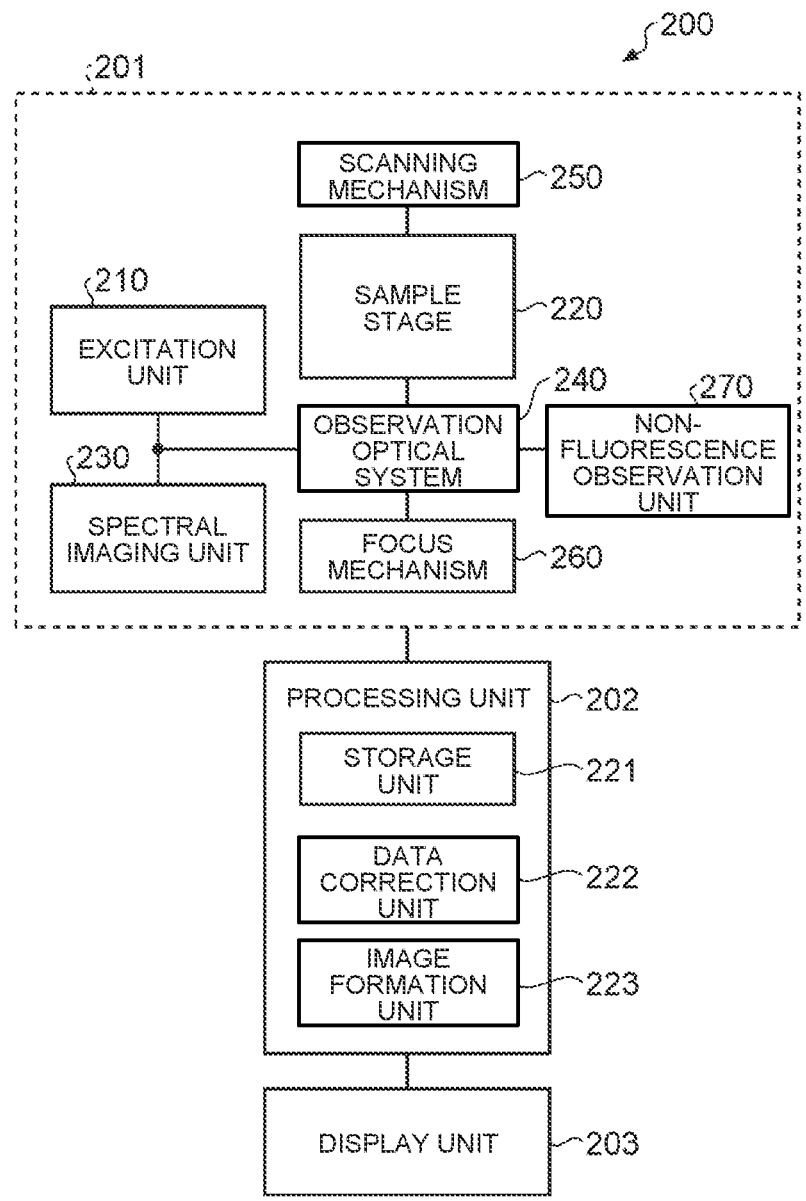
FIG. 14 is a block diagram illustrating a schematic configuration example of an optical measurement device (system) according to a second embodiment.

FIG. 14 is a block diagram illustrating a schematic configuration example of an optical measurement device (system) according to a second embodiment.

As illustrated in FIG. 14, an optical measurement device 200 of the present embodiment includes an observation unit 201. The observation unit 201 has an excitation unit 210 that irradiates a pathological specimen (pathological sample) with a plurality of line illuminations having different wavelengths disposed in parallel with different axes, a sample stage 220 that supports the pathological specimen, and a spectral imaging unit 230 that acquires a fluorescence spectrum (spectral data) of the pathological specimen excited in a line shape.

The optical measurement device 200 further includes a processing unit 202 corresponding to the signal acquisition system 1 and the analysis system 2 in the first embodiment. The processing unit 202 typically forms an image (corresponding to a spectral image) of the pathological specimen or outputs a distribution of the fluorescence spectrum, on the basis of the fluorescence spectrum of the pathological specimen (hereinafter, also referred to as a sample S) acquired by the observation unit 201. Here, the image refers to a composition ratio such as autofluorescence derived from a dye or a sample constituting the spectrum, a luminance distribution in a specific wavelength band of a waveform converted into RGB (red, green, and blue) colors, and the like.

The excitation unit 210 and the spectral imaging unit 230 are connected to the sample stage 220 via an observation optical system 240 such as an objective lens. The observation optical system 240 has a function of following an optimum focus by a focus mechanism 260. A non-fluorescence observation unit 270 for dark field observation, bright field observation, or the like may be connected to the observation optical system 240. The focus mechanism 260, the non-fluorescence observation unit 270, and the like are connected to a control unit (a personal computer (PC) or the like) that performs storage, control, and calculation processing.

The excitation unit 210 includes a plurality of light sources each capable of outputting excitation light having a different wavelength. The plurality of light sources typically includes a light emitting diode (LED), a laser diode (LD), a mercury lamp, and the like, and each of the light sources is line-illuminated and irradiates the sample S on the sample stage 220 with the light.

The sample S is typically formed by a slide including an observation target such as a tissue section, but it is needless to say that the sample S may be other materials. The sample S is dyed with a plurality of fluorescent dyes. The observation unit 201 enlarges the sample S at a desired magnification and observes the sample S. A plurality of line illuminations are disposed, and a plurality of photographing areas of the spectral imaging unit 230 are disposed so as to overlap with the respective illumination areas. The two line illuminations are disposed in parallel to be separated from each other. A longitudinal direction of each line illumination is defined as an X-axis direction, and an arrangement direction is defined as a Y-axis direction.

The wavelength constituting the first line illumination and the wavelength constituting the second line illumination are different from each other. The linear fluorescence excited by the line illumination is observed in the spectral imaging unit 230 via the observation optical system 240.

The spectral imaging unit 230 has an observation slit having a plurality of slit portions through which the fluorescence excited by the plurality of line illuminations can pass, and at least one imaging element (corresponding to the image sensor 34) capable of individually receiving the fluorescence having passed through the observation slit. As the imaging element, a two-dimensional imager such as a charge coupled device (CCD) or a complementary metal oxide semiconductor (CMOS) is adopted. By disposing the observation slit on an optical path, the fluorescence spectra excited by the respective lines can be detected without overlapping.

The spectral imaging unit 230 acquires spectral data $(x, \lambda)$ of fluorescence using a pixel array in one direction (for example, a vertical direction) of the imaging element as a wavelength channel, from each line illumination. The acquired spectral data $(x, \lambda)$ is recorded in the processing unit 202 in a state in which the spectral data being spectral data excited from which excitation wavelength is associated.

The processing unit 202 can be realized by hardware elements used in a computer such as a central processing unit (CPU), a random access memory (RAM), and a read only memory (ROM), and necessary software. Instead of or in addition to the CPU, a programmable logic device (PLD) such as a field programmable gate array (FPGA), a digital signal processor (DSP), an application specific integrated circuit (ASIC), or the like may be used.

The processing unit 202 has a storage unit 221 that stores spectral data indicating a correlation between the wavelengths of the plurality of line illuminations and the fluorescence received by the imaging element. A storage device such as a nonvolatile semiconductor memory or a hard disk drive is used in the storage unit 221, and a standard spectrum of autofluorescence related to the sample S and a standard spectrum of a single dye dyeing the sample S are stored in advance. The spectral data $(x, \lambda)$ received by the imaging element is stored in the storage unit 221, for example.

The observation unit 201 further includes a scanning mechanism 250 that scans the sample stage 220 with the plurality of line illuminations in the Y-axis direction, that is, the arrangement direction of the line illuminations. By using the scanning mechanism 250, dye spectra (fluorescence spectra) that are spatially separated by $\Delta y$ on the sample S and are excited at different excitation wavelengths can be continuously recorded in the Y-axis direction. In this case, for example, a photographing region is divided into a plurality of parts in the X-axis direction, and an operation of scanning the sample S in the Y-axis direction, moving in the X-axis direction, and performing scanning in the Y-axis direction is repeated. Spectral images from the sample excited by several excitation wavelengths can be photographed in a single scan.

In the scanning mechanism 250, typically, the sample stage 220 is scanned in the Y-axis direction, but a plurality of line illuminations may be scanned in the Y-axis direction by a galvanometer mirror disposed in the middle of the optical system. Finally, three-dimensional data of $(X, Y, \lambda)$ is acquired for each of the plurality of line illuminations. Since the three-dimensional data derived from each line illumination is data whose coordinates have been shifted by $\Delta y$ with respect to the Y axis, the three-dimensional data is corrected on the basis of a value of $\Delta y$ recorded in advance or $\Delta y$ calculated from the output of the imaging element 34 and output.

In the above example, although the number of line illuminations as the excitation light is two, the present disclosure is not limited thereto, and the number of line illuminations may be three, four, or five or more. In addition, each line illumination may include a plurality of excitation wavelengths selected so that color separation performance is not degraded as much as possible. In addition, when the excitation light source includes a plurality of excitation wavelengths even if there is one line illumination, and each excitation wavelength and row data obtained by the imaging element are recorded in association with each other, separability in the case of being disposed in parallel with different axes is not obtained, but multicolor spectra can be obtained.

An image formation unit 223 forms a fluorescence image of the sample S on the basis of spectral data stored in the storage unit 221 (or spectral data corrected by a data correction unit 222) and an interval corresponding to an inter-axis distance $(\Delta y)$ of an excitation line.

Since the three-dimensional data derived from each line illumination is data whose coordinates have been shifted by $\Delta y$ with respect to the Y axis, the three-dimensional data is corrected on the basis of a value of $\Delta y$ recorded in advance or $\Delta y$ calculated from the output of the imaging element and output.

The image formation unit 223 executes processing (stitching) for combining photographed images into one large image. As a result, a pathological image regarding the multiplexed sample S can be acquired. The formed fluorescence image is output to a display unit 203.

Further, the image formation unit 223 separates and calculates component distributions of the autofluorescence and the dye of the sample S from the photographed spectral data (measurement spectrum), on the basis of each standard spectrum of the autofluorescence and the single dye of the sample S stored in advance in the storage unit 221. As a calculation method, a least squares method, a weighted least squares method, or the like can be adopted, and a coefficient in which photographed spectral data becomes a linear sum of the standard spectra is calculated. The calculated coefficient distribution is stored in the storage unit 221, is output to the display unit 203, and is displayed as an image.

As described above, similarly to the first embodiment, with respect to the DPI, a light detection unit can be used as the image sensor 34. Further, the multichannel analysis or the virtual filter function can be similarly applied to the DPI.

Although the embodiments of the present disclosure have been described above, the technical scope of the present disclosure is not limited to the above-described embodiments, and various changes can be made without departing from the gist of the present disclosure. Further, components of different embodiments and modifications may be appropriately combined.

Further, the effects of each embodiment described in the present specification are merely examples and are not limited, and other effects may be provided.

Note that the present technology can also take the following configurations.

(1)
An optical measurement device, comprising:
  a spectral optical system that disperses fluorescence emitted from a biological specimen; and
  an image sensor that receives the fluorescence dispersed by the spectral optical system and generates fluorescence information, wherein
  the image sensor is divided into a plurality of regions that receive different wavelength components of the fluorescence and generate fluorescence information for each of the wavelength components.

(2)
The optical measurement device according to (1), wherein the fluorescence information is image data including a value obtained by adding pixel values for the respective pixels of the image sensor for each of the regions, or a pixel value for each of the pixels.

(3)
The optical measurement device according to (1) or (2), further comprising:
  a signal acquisition unit that evaluates the fluorescence information generated by the image sensor.

(4)
The optical measurement device according to (3), wherein the signal acquisition unit divides the fluorescence information into a plurality of channel regions arranged along a spectral direction of the fluorescence dispersed by the spectral optical system, adds pixel values of the plurality of channel regions, and calculates an evaluation value of the fluorescence information.

(5)
The optical measurement device according to (3), wherein the signal acquisition unit adds pixel values of one or more filter regions in the fluorescence information and calculates an evaluation value of the fluorescence information.

(6)
The optical measurement device according to any one of (1) to (5), wherein
  the spectral optical system includes a prism that disperses the fluorescence in a predetermined direction, and a width of a first region of the plurality of regions in a direction corresponding to the predetermined direction, a first wavelength component of the fluorescence being incident on the first region, is smaller than a width of a second region of the plurality of regions in the direction corresponding to the predetermined direction, a second wavelength component of the fluorescence longer than the first wavelength component being incident on the second region.

(7)
The optical measurement device according to (3), further comprising:
  an analysis unit that analyzes the biological specimen on the basis of an evaluation result of the fluorescence information by the signal acquisition unit.

(8)
The optical measurement device according to (2), wherein the image sensor includes
  a plurality of photoelectric conversion elements that are arranged in a matrix, and
  a detection circuit that generates the pixel values constituting the fluorescence information on the basis of charges generated in each of the photoelectric conversion elements.

(9)
The optical measurement device according to any one of (1) to (8), further comprising:
  an excitation light source that irradiates the biological specimen with excitation light having a predetermined wavelength.

(10)
The optical measurement device according to (9), further comprising:
  a flow path through which the biological specimen flows, wherein
  the excitation light source irradiates a predetermined region in the flow path with the excitation light.

(11)
The optical measurement device according to any one of (1) to (10), further comprising:
  an excitation light source that emits excitation light having a predetermined wavelength;
  a stage on which the biological specimen is placed; and
  a scanning mechanism that controls a positional relation between the stage and the excitation light source such that the excitation light scans the biological specimen on the stage.

(12)
An optical measurement system comprising:
  a spectral optical system that disperses fluorescence emitted from a biological specimen;
  an image sensor that receives the fluorescence dispersed by the spectral optical system and generates fluorescence information;
  a signal acquisition unit that evaluates the fluorescence information generated by the image sensor; and
  an analysis unit that analyzes the biological specimen on the basis of an evaluation result of the fluorescence information by the signal acquisition unit, wherein
  the image sensor includes a plurality of regions that receive different wavelength components of the fluorescence and generate fluorescence information for each of the wavelength components.

REFERENCE SIGNS LIST

1 SIGNAL ACQUISITION SYSTEM
2 ANALYSIS SYSTEM
11 FLOW CYTOMETER
31 FLOW CELL
32 EXCITATION LIGHT SOURCE
33 PHOTODIODE
34 IMAGE SENSOR
35, 36 CONDENSER LENS
37 SPECTRAL OPTICAL SYSTEM
371 OPTICAL ELEMENT
51 SAMPLE TUBE
52 SAMPLE FLOW
53 SPECIMEN
71 EXCITATION LIGHT
72 IRRADIATION SPOT
73 FORWARD SCATTERED LIGHT
74 FLUORESCENCE
75 DISPERSED LIGHT
91 PIXEL ARRAY UNIT
92 CONNECTION UNIT
93 DETECTION CIRCUIT
93A, 93B DETECTION CIRCUIT ARRAY
94 PIXEL DRIVE CIRCUIT
95 LOGIC CIRCUIT
96 OUTPUT CIRCUIT
101 PIXEL
111 PHOTODIODE
112 ACCUMULATION NODE
113 TRANSFER TRANSISTOR
114 AMPLIFICATION TRANSISTOR
116 RESET TRANSISTOR
118 POWER SUPPLY
121 ROW DRIVE CIRCUIT
122 CONSTANT CURRENT CIRCUIT
124 VERTICAL SIGNAL LINE
200 OPTICAL MEASUREMENT DEVICE
201 OBSERVATION UNIT
202 PROCESSING UNIT
203 DISPLAY UNIT
210 EXCITATION UNIT
220 SAMPLE STAGE
230 SPECTRAL IMAGING UNIT
240 OBSERVATION OPTICAL SYSTEM
250 SCANNING MECHANISM
260 FOCUS MECHANISM
270 NON-FLUORESCENCE OBSERVATION UNIT
221 STORAGE UNIT
222 DATA CORRECTION UNIT
223 IMAGE FORMATION UNIT
CH1 to CH32 CHANNEL REGION
F1 to F4 VIRTUAL FILTER
G1 SPECTRAL IMAGE
H1 ROW DIRECTION
V1 COLUMN DIRECTION

The invention claimed is:

1. An optical measurement device, comprising:
a spectral optical system configured to disperse fluorescence emitted from a biological specimen;
an image sensor configured to:
receive the fluorescence dispersed by the spectral optical system; and
generate fluorescence information, wherein
the image sensor is divided into a plurality of regions,
each region of the plurality of regions is configured to receive a different wavelength component of wavelength components of the fluorescence, wherein the generated fluorescence information comprises information corresponding to the received different wavelength component of the wavelength components, and
the fluorescence information is image data including a value obtained by addition of pixel values, for pixels of the image sensor, for each of the plurality of regions;
a signal acquisition unit configured to calculate, based on the addition of the pixel values for each of the plurality of regions, an evaluation value of the fluorescence information; and
an analysis unit configured to:
analyze the biological specimen based on the evaluation value of the fluorescence information by the signal acquisition unit; and
display the evaluation value.

2. The optical measurement device according to claim 1, wherein the signal acquisition unit is further configured to:
divide the fluorescence information into a plurality of channel regions along a spectral direction of the fluorescence dispersed by the spectral optical system,
wherein the plurality of channel regions corresponds to the plurality of regions.

3. The optical measurement device according to claim 1, wherein the signal acquisition unit is further configured to add pixel values of one or more filter regions in the fluorescence information.

4. The optical measurement device according to claim 1, wherein
the spectral optical system includes a prism configured to disperse the fluorescence in a specific direction, and
a width of a first region of the plurality of regions in a direction corresponding to the specific direction is smaller than a width of a second region of the plurality of regions in the direction corresponding to the specific direction,
a first wavelength component of the fluorescence is incident on the first region, and
a second wavelength component of the fluorescence longer than the first wavelength component is incident on the second region.

5. The optical measurement device according to claim 1, wherein
the image sensor includes:
a plurality of photoelectric conversion elements that are in a matrix, and
a detection circuit configured to generate the pixel values constituting the fluorescence information, based on charges generated in each of the plurality of photoelectric conversion elements.

6. The optical measurement device according to claim 1, further comprising:
an excitation light source configured to irradiate the biological specimen with excitation light having a specific wavelength.

7. The optical measurement device according to claim 6, further comprising:
a flow path through which the biological specimen flows, wherein
the excitation light source is further configured to irradiate a specific region in the flow path with the excitation light.

8. The optical measurement device according to claim 1, further comprising:

an excitation light source configured to emit excitation light having a specific wavelength;

a stage on which the biological specimen is placed; and a scanning mechanism configured to control a positional relation between the stage and the excitation light source such that the excitation light scans the biological specimen on the stage.

9. The optical measurement device according to claim 1, wherein the analysis unit is further configured to acquire at least one of a type, a size, or a structure of the biological specimen based on the evaluation value.

10. An optical measurement system, comprising:

a spectral optical system configured to disperse fluorescence emitted from a biological specimen;

an image sensor configured to:

receive the fluorescence dispersed by the spectral optical system; and generate fluorescence information, wherein
the image sensor includes a plurality of regions,
each region of the plurality of regions is configured to receive a different wavelength component of wavelength components of the fluorescence, wherein the generated fluorescence information comprises information corresponding to the received different wavelength component of the wavelength components, and
the fluorescence information is image data including a value obtained by addition of pixel values, for pixels of the image sensor, for each of the plurality of regions;

a signal acquisition unit configured to calculate, based on the addition of the pixel values for each of the plurality of regions, an evaluation value of the fluorescence information; and an analysis unit configured to:
analyze the biological specimen based on the evaluation value of the fluorescence information by the signal acquisition unit; and
display the evaluation value.

* * * * *